(12) United States Patent
Reddy et al.

(10) Patent No.: US 10,821,288 B2
(45) Date of Patent: Nov. 3, 2020

(54) CARDIAC PACEMAKER WITH PACING PULSE ENERGY ADJUSTMENT BASED ON SENSED HEART RATE

(71) Applicant: CARDIAC PACEMAKERS, INC., St. Paul, MN (US)

(72) Inventors: G. Shantanu Reddy, Minneapolis, MN (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 188 days.

(21) Appl. No.: 15/938,719

(22) Filed: Mar. 28, 2018

(65) Prior Publication Data

US 2018/0280702 A1    Oct. 4, 2018

Related U.S. Application Data

(60) Provisional application No. 62/480,784, filed on Apr. 3, 2017.

(51) Int. Cl.

| | | |
|---|---|---|
| *A61N 1/365* | (2006.01) | |
| *A61N 1/372* | (2006.01) | |
| *A61N 1/375* | (2006.01) | |
| *A61N 1/37* | (2006.01) | |
| *A61N 1/362* | (2006.01) | |

(52) U.S. Cl.
CPC ....... *A61N 1/36592* (2013.01); *A61N 1/3621* (2013.01); *A61N 1/36507* (2013.01); *A61N 1/36578* (2013.01); *A61N 1/36585* (2013.01); *A61N 1/371* (2013.01); *A61N 1/3756* (2013.01); *A61N 1/37205* (2013.01); *A61N 1/37211* (2013.01); *A61N 1/37512* (2017.08); *A61N 1/36542* (2013.01)

(58) Field of Classification Search
None
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| 4,142,530 A | 3/1979 | Wittkampf |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Kennedy Schaetzle
(74) *Attorney, Agent, or Firm* — Seager, Tufte & Wickhem LLP

(57) ABSTRACT

Implantable medical devices (IMD) such as a cardiac pacemakers may include a sensor and electrodes. In some cases, the IMD may include electronics to use the sensor to determine the heart rate of a patient's heart. The electronics may use the electrodes to deliver pacing pulses to the heart at a first energy level if the heart rate is below a threshold and pace the heart at an enhanced energy level if the heart rate is above the threshold.

20 Claims, 12 Drawing Sheets

(56) References Cited

U.S. PATENT DOCUMENTS

| | | |
|---|---|---|
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,128,529 A * | 10/2000 | Esler ............ A61N 1/3622 607/4 |
| 6,141,581 A | 10/2000 | Olson et al. |
| 6,141,588 A | 10/2000 | Cox et al. |

(56) References Cited

U.S. PATENT DOCUMENTS

| | | |
|---|---|---|
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 * | 5/2005 | Ousdigian ............ A61N 1/3962 607/4 |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |

(56) References Cited

U.S. PATENT DOCUMENTS

| | | |
|---|---|---|
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |

(56) References Cited

U.S. PATENT DOCUMENTS

| | | |
|---|---|---|
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 * | 6/2014 | Greenhut ............ A61N 1/37288 607/4 |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |

(56) References Cited

U.S. PATENT DOCUMENTS

| | | | |
|---|---|---|---|
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,323,182 B2 * | 6/2019 | Jun .................. B82Y 30/00 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0039422 A1 * | 2/2004 | Russie .................. A61N 1/368 607/9 |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |

(56) References Cited

U.S. PATENT DOCUMENTS

| | | |
|---|---|---|
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |

(56) References Cited

U.S. PATENT DOCUMENTS

| | | |
|---|---|---|
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Mates |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |

(56) References Cited

U.S. PATENT DOCUMENTS

| | | |
|---|---|---|
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0228701 A1 | 8/2016 | Huelskamp et al. |
| 2016/0228718 A1 | 8/2016 | Koop |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0072202 A1 | 3/2017 | Kane et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2950881 A1 | 12/2015 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 2012500050 A | 1/2012 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006069215 A2 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |

(56) References Cited

FOREIGN PATENT DOCUMENTS

| WO | 2013184787 A1 | 12/2013 |
| WO | 2014120769 A1 | 8/2014 |
| WO | 2016118814 A1 | 7/2016 |

OTHER PUBLICATIONS

International Search Report and Written Opinion for Application No. PCT/US2018/024875, 15 pages, dated Jul. 5, 2018.
Hügl B et al: "Incremental programming of atrial anti-tachycardia pacing therapies in bradycardia-indicated patients: effects on therapy efficacy and atrial tachyarrhythmia burden" EUROPACE, W.B. Saunders, GB, vol. 5, No. 4, Oct. 1, 2003 (Oct. 1, 2003), pp. 403-409, XP002559877, ISSN: 1099-5129, DOI: 10.1016/S1099-5129(03) 00082-5 the whole document.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering,vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.

\* cited by examiner

CARDIAC PACEMAKER WITH PACING PULSE ENERGY ADJUSTMENT BASED ON SENSED HEART RATE

CROSS REFERENCE TO RELATED APPLICATIONS

This application claims the benefit of U.S. Provisional Patent Application Ser. No. 62/480,784 filed on Apr. 3, 2017, the disclosure of which is incorporated herein by reference.

TECHNICAL FIELD

The disclosure relates generally to implantable medical devices, and more particularly to implantable cardiac pacemakers that have a post shock pacing capability.

BACKGROUND

Implantable medical devices (IMDs) are commonly used to perform a variety of functions, such as monitor one or more conditions and/or delivery therapy to a patient. In some cases, IMDs may treat patients suffering from various heart conditions that may result in a reduced ability of the heart to deliver sufficient amounts of blood to a patient's body. Some heart conditions may lead to low heart rates (e.g. bradycardia), while others may lead to rapid, irregular, and/or inefficient heart contractions (tachycardia). To help alleviate these and other conditions, various devices (e.g., pacemakers, defibrillators, etc.) can be implanted into a patient's body. When so provided, such devices can monitor and provide therapy, such as electrical stimulation therapy, to the patient's heart to help the heart operate in a more normal, efficient and/or safe manner. In some cases, an IMD may be configured to deliver pacing and/or defibrillation therapy to a patient's heart. In other cases, a patient may have multiple implanted devices that cooperate to deliver pacing and/or defibrillation therapy to the patient's heart.

In some instances, an IMD may perform demand pacing to help ensure that the heart rate of a patient does not fall below a lower heart rate threshold. When performing demand pacing, the IMD may pace the heart at the lower heart rate threshold when the intrinsic heart rate falls below the lower heart rate threshold. In some instances, the heart may be susceptible to cardiac fibrillation, which may be characterized by rapid, irregular, and/or inefficient heart contractions. When this happens, an Implantable Cardioverter Defibrillator (ICD) can be used to deliver a shock to the heart of the patient to defibrillate the heart. The heart typically stops beating for a moment in response to a delivered shock event, but then resumes in a normal rhythm. Often post-shock pacing pulses are delivered after the shock event to help bring the heart back into the normal rhythm. In some cases, the post-shock pacing pulses are delivered at a higher amplitude than the pacing pulses that are used during demand pacing. In some instances, an ICD may deliver both demand pacing and defibrillation shock therapy. In other instances, an IMD may deliver demand pacing while a separate ICD may deliver defibrillation shock therapy.

What would be desirable is an IMD that can deliver demand pacing, and can also anticipate a coming shock event from a remote ICD based on a detected heart rate condition, and then on its own increasing the energy level for subsequently delivered pacing pulses over a temporarily period of time. Such an IMD may, for example, deliver post shock pacing pulses with increased energy levels without requiring communication between the IMD and the remote ICD.

SUMMARY

The disclosure relates generally to implantable medical devices, and more particularly to implantable cardiac pacemakers that have a post shock pacing capability. While a Leadless Cardiac Pacemaker (LCP) is used as an example implantable cardiac pacemaker, it should be recognized that the disclosure may be applied to any suitable implantable medical device as desired.

In an example of the disclosure, a cardiac pacemaker that is free from an Implantable Cardioverter Defibrillator (ICD) may include one or more sensors for sensing one or more physiological parameters of a patient, and two or more pacing electrodes for delivering pacing pulses to the heart of the patient. Electronics operatively coupled to the one or more sensors and the two or more pacing electrodes may be configured to determine a heart rate of the patient based at least in part on the one or more physiological parameters sensed by the one or more sensors and may pace the heart of the patient via the two or more pacing electrodes in a manner that attempts to keep the heart rate of the patient from falling below a demand heart rate threshold. If the heart rate is below an upper heart rate threshold, the pacing pulses may be delivered at a capture pacing energy level. If the heart rate rises above the upper heart rate threshold, the pacing pulses may be temporarily delivered at an enhanced energy level above the capture pacing energy level for a period of time, and after the period of time, the pacing pulses may again be delivered at the capture energy level. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what is deemed appropriate therapy at any given time.

Alternatively or additionally to any of the embodiments above, the one or more sensors may comprise two or more sensing electrodes, and at least one of the physiological parameters may comprise a cardiac electrical signal.

Alternatively or additionally to any of the embodiments above, at least one of the two or more sensing electrodes may be one of the pacing electrodes.

Alternatively or additionally to any of the embodiments above, the one or more sensors may comprise an accelerometer, and at least one of the physiological parameters may comprise one or more of a heart motion and a heart sound.

Alternatively or additionally to any of the embodiments above, the heart rate determined by the electronics may be an average heart rate of "n" previous heart beats, wherein "n" may be an integer greater than one.

Alternatively or additionally to any of the embodiments above, the pacing pulses may have a first amplitude and first pulse width at the capture pacing energy level, and a second amplitude and second pulse width at the enhanced energy level, wherein the second amplitude may be greater than the first amplitude and the second pulse width may be the same as the first pulse width.

Alternatively or additionally to any of the embodiments above, the pacing pulses may have a first amplitude and first pulse width at the capture pacing energy level, and a second amplitude and second pulse width at the enhanced energy level, wherein the second amplitude may be the same as the first amplitude and the second pulse width may be greater than the first pulse width.

Alternatively or additionally to any of the embodiments above, the pacing pulses may have a first amplitude and first pulse width at the capture pacing energy level, and a second amplitude and second pulse width at the enhanced energy level, wherein the second amplitude may be greater than the first amplitude and the second pulse width may be greater than the first pulse width.

Alternatively or additionally to any of the embodiments above, the period of time may be a predetermined period of time.

Alternatively or additionally to any of the embodiments above, the predetermined period of time may be programmable.

Alternatively or additionally to any of the embodiments above, the period of time may be greater than 3 minutes.

Alternatively or additionally to any of the embodiments above, the period of time may be less than 1 hour.

Alternatively or additionally to any of the embodiments above, further comprising a communication module, wherein the electronics can receive commands from a remote device via the communication module, and wherein in response to receive an ATP command, the electronics may be configured to deliver a burst of ATP pacing pulses at the enhanced energy level.

Alternatively or additionally to any of the embodiments above, the cardiac pacemaker may be a leadless cardiac pacemaker (LCP) that may be configured to be implanted within a chamber of the heart of the patient.

In another example of the disclosure, a leadless cardiac pacemaker (LCP) may comprised a housing, and a plurality of electrodes for sensing electrical signals emanating from outside of the housing. An energy storage module may be disposed within the housing. The LCP may further include a pulse generator for delivering pacing pulses via two or more of the plurality of electrodes, wherein the pulse generator may be capable of changing an energy level of the pacing pulses. A control module disposed within the housing may be operatively coupled to the pulse generator and at least two of the plurality of electrodes. The control module may be configured to receive one or more cardiac signals via two or more of the plurality of electrodes, determine a heart rate based at least in part on the received one or more cardiac signals, instruct the pulse generator to pace the heart with pacing pulses at a capture pacing energy level in a manner that attempts to keep the heart rate from falling below a demand heart rate threshold, determine if the heart rate rises above an upper heart rate threshold, and in response to determining that the heart rate has risen above the upper heart rate threshold, instruct the pulse generator to increase the energy level of the pacing pulses to an enhanced energy level for a period of time, and after the period of time, instruct the pulse generator to decrease the energy level of the pacing pulses back to the capture pacing energy level. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what is deemed appropriate therapy at any given time.

Alternatively or additionally to any of the embodiments above, the pulse generator may change an amplitude of the pacing pulses to increase the energy level of the pacing pulses to the enhanced energy level.

Alternatively or additionally to any of the embodiments above, the pulse generator may change a pulse width of the pacing pulses to increase the energy level of the pacing pulses to the enhanced energy level.

Alternatively or additionally to any of the embodiments above, the pulse generator may change an amplitude and a pulse width of the pacing pulses to increase the energy level of the pacing pulses to the enhanced energy level.

In another example of the disclosure, a method for pacing a heart of a patient may comprise determining a heart rate of the patient, and pacing the heart of the patient in a manner that attempts to keep the heart rate of the patient from falling below a demand heart rate threshold. If the heart rate is below an upper heart rate threshold, pacing pulses may be delivered at a capture pacing energy level. If the heart rate rises above the upper heart rate threshold, pacing pulses may temporarily be delivered at an enhanced energy level above the capture pacing energy level for a period of time, and after the period of time, the pacing pulses may again be delivered at the capture pacing energy level. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what is deemed appropriate therapy at any given time.

Alternatively or additionally to any of the embodiments above, the heart rate may be determined by an average heart rate of "n" previous heart beats, wherein "n" may be an integer greater than one.

The above summary of some illustrative embodiments is not intended to describe each disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which.

Figure 1:
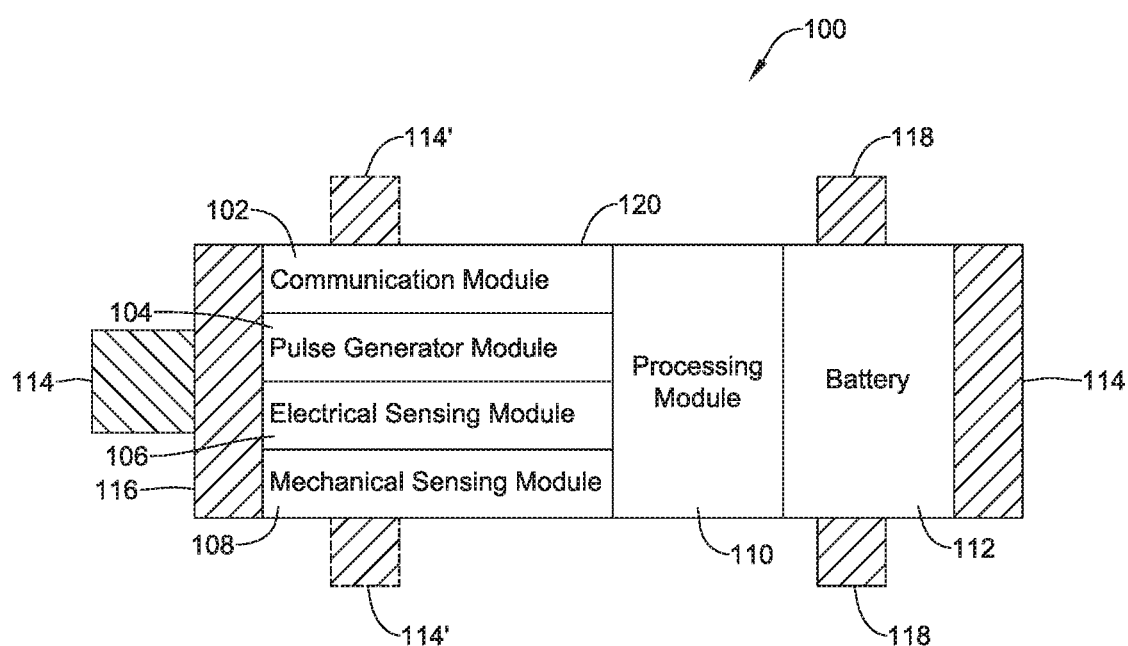
FIG. 1 is a schematic block diagram of an illustrative LCP, in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 depicts an illustrative cardiac pacemaker (e.g., a leadless cardiac pacemaker (LCP) 100) that may be implanted into a patient and may operate to deliver appropriate therapy to the heart, such as to deliver demand pacing therapy (e.g. for bradycardia), anti-tachycardia pacing (ATP) therapy, post-shock pacing therapy, cardiac resynchronization therapy (CRT) and/or the like. While a Leadless Cardiac Pacemaker (LCP) is used as an example implantable cardiac pacemaker, it should be recognized that the disclosure may be applied to any suitable implantable medical device as desired.

As can be seen in FIG. 1, the LCP 100 may be a compact device with a control module or electronics including all of its components housed within or directly on a housing 120. In some cases, the LCP 100 may be considered as being an example of an implantable medical device (IMD). In the example shown in FIG. 1, the control module or electronics of the LCP 100 may include a communication module 102, a pulse generator module 104, an electrical sensing module 106, a mechanical sensing module 108, a processing module 110, a battery 112, and an electrode arrangement 114. The control module or electronics of the LCP 100 may include more or less modules, depending on the application.

The electrical sensing module 106 may be configured to sense one or more physiological parameters of a patient. In some examples, the physiological parameters may include the cardiac electrical activity of the heart. For example, the electrical sensing module 106 may be connected to sensors 118 and the electrical sensing module 106 may be configured to sense the physiological parameters of the patient via the sensors 118. In some examples, the electrical sensing module 106 may be connected to electrodes 114/114', and the electrical sensing module 106 may be configured to sense one or more of the physiological parameters of the patient, including cardiac electrical signals, via the electrodes 114/114'. In this case, the electrodes 114/114' are the sensors.

According to various embodiments, the physiological parameters may be indicative of the state of the patient and/or the state of the heart of the patient. For example, in some cases, the physiological parameters may include temperature (e.g., blood temperature, body tissue temperature, etc.), respiration activity, cardiac electrical signals, etc. In addition, in some examples, the cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' and/or sensors 118 may represent ventricular cardiac electrical signals. In some cases, the LCP 100 may be configured to detect cardiac electrical signals from other chambers (e.g. far field), such as the P-wave from the atrium.

In some examples, the mechanical sensing module 108, when provided, may be configured to sense one or more physiological parameters of the patient. For example, in certain embodiments, the mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensor that is configured to detect one or more mechanical/chemical physiological parameters of the patient (e.g., heart motion, heart sound, etc.). The mechanical sensing module 108 may receive and measure the physiological parameters. Both the electrical sensing module 106 and the mechanical sensing module 108 may be connected to a processing module 110, which may provide signals representative of the sensed parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 and may be exposed to the tissue and/or blood surrounding the LCP 100. In some cases, depending on the sensor type, the sensors 118 may be internal to the housing or exposed to the tissue and/or blood surrounding the LCP 100. In some cases, the electrodes 114 may be generally disposed on either end of the LCP 100. In some examples, the electrodes 114/114' and sensors 118 may be in electrical communication with one or more of the modules 102, 104, 106, 108, and 110. The electrodes 114/114' and/or sensors 118 may be supported by the housing 120. In some examples, the electrodes 114/114' and/or sensors 118 may be connected to the housing 120 through short connecting wires such that the electrodes 114/114' and/or sensors 118 are not directly secured relative to the housing 120 but rather located on a tail that is connected the housing. In examples where the LCP 100 includes one or more electrodes 114', the electrodes 114' may in some cases be disposed on the sides of the LCP 100, which may increase the number of electrodes by which the LCP 100 may sense physiological parameters, deliver electrical stimulation, and/or communicate with an external medical device. The electrodes 114/114' and/or sensors 118 can be made up of one or more biocompatible conductive materials such as various metals or alloys that are known to be safe for implantation within a human body. In some instances, the electrodes 114/114' and/or sensors 118 connected to the LCP 100 may have an insulative portion that electrically isolates the electrodes 114/114' and/or sensors 118 from adjacent electrodes/sensors, the housing 120, and/or other parts of the LCP 100.

The processing module 110 may include electronics that is configured to control the operation of the LCP 100. For example, the processing module 110 may be configured to receive electrical signals from the electrical sensing module 106 and/or the mechanical sensing module 108. Based on the received signals, the processing module 110 may determine, for example, a heart rate of the patient, abnormalities in the operation of the heart, etc. Based on the determined conditions, the processing module 110 may control the pulse generator module 104 to generate and deliver pacing pulses in accordance with one or more therapies to treat the determined conditions. The processing module 110 may further receive information from the communication module 102. In some examples, the processing module 110 may use such received information to help determine the current conditions of the patient, determine whether an abnormality is occurring given the current condition, and/or to take a particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. In some cases, the pre-programmed chip may implement a state machine that performs the desired functions. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some instances, the battery 112 may a rechargeable battery, which may help increase the useable lifespan of the LCP 100. In still other examples, the battery 112 may be some other type of power source, such as a fuel cell or the like, as desired.

In the example shown in FIG. 1, the pulse generator module 104 may be electrically connected to the electrodes 114/114'. In some cases, the sensors 118 may also have electrical stimulation functionality and may be electrically connected to the pulse generator module 104 when desired. Said another way, one or more of the electrodes 114/114' may function as a sensor 118 electrode, such as for sensing cardiac electrical signals. In some cases, the LCP 100 may have a controllable switch that connects one or more of the electrodes 114/114' to the pulse generator module 104 when the pulse generator module 104 delivers a pacing pulse, and may connect one or more of the electrodes 114/114' to the electrical sensing module 106 when the pulse generator module 104 is not delivering a pacing pulse.

The pulse generator module 104 may be configured to generate electrical stimulation signals. For example, the pulse generator module 104 may generate and deliver electrical pacing pulses by using energy stored in the battery 112 within the LCP 100 and deliver the generated pacing pulses via the electrodes 114, 114' and/or sensors 118. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated pacing pulses via the electrodes 114, 114', and/or sensors 118. In at least some examples, the pulse generator 104 of the LCP 100 may include switching circuitry to selectively connect one or more of the electrodes 114, 114' and/or sensors 118 to the pulse generator 104 in order to select which of the electrodes 114/114' and/or sensors 118 (and/or other electrodes) the pulse generator 104 uses to deliver the electrical stimulation therapy. The pulse generator module 104 may be configured to deliver pacing pulses at two or more different energy levels. This may be accomplished by controlling the amplitude, pulse width, pulse shape and/or any other suitable characteristic of the pacing pulses.

According to various embodiments, the sensors 118 may be configured to sense one or more physiological parameters of a patient and send a signal to the electrical sensing module 106 and/or the mechanical sensing module 108. For example, the physiological parameters may include a cardiac electrical signal and the sensors 118 may send a response signal to the electrical sensing module 106. In some examples, one or more of the sensors 118 may be an accelerometer and the physiological parameters may alternatively or additionally include heart motion and/or heart sounds and the sensors 118 may send a corresponding signal to the mechanical sensing module 108. Based on the sensed signals, the sensing modules 106 and/or 108 may determine or measure one or more physiological parameters, such as heart rate, respiration rate, activity level of the patient and/or any other suitable physiological parameters. The one or more physiological parameters may then be passed to the processing module 110.

In some cases, the intrinsic heart rate of the patient may reach and/or fall below a demand heart rate threshold and into a "Normal Demand Zone". In this case, the processing module 110 may perform demand pacing by instructing the pulse generator module 104 to deliver pacing pulses at a set energy level using the electrodes 114/114' in a manner that attempts to keep the heart rate of the patient from falling below the demand heart rate threshold. The demand heart rate threshold may be a fixed heart rate such as a lower rate limit, or may be a dynamic heart rate that is dependent on the activity level of the patient. In order to help conserve battery power, the pacing pulses may be delivered at a capture pacing energy level, which is above the capture threshold of the heart but less than the maximum allowed pacing energy level.

In some cases, the intrinsic heart rate may rise to and/or above a normal heart rate upper threshold and into an "ATP Zone". In this case, the intrinsic heart rate observed may be a fast but regular rhythm, such as that observed during ventricular tachycardia. Similar to the demand heart rate threshold, the normal heart rate upper threshold may be a fixed rate or a dynamic heart rate that is dependent on the activity level of the patient. In response to the intrinsic heart rate reaching and/or exceeding the normal heart rate upper threshold, the processing module 110 may be configured to automatically perform anti-tachyarrhythmia-pacing (ATP) therapy by instructing the pulse generator module 104 to deliver ATP pulses at the capture pacing energy level (or an enhanced level if desired). Note, in this case, the LCP 100 may autonomously initiate ATP therapy based on the detected heart rate without having to first receive a command from another medical device notifying the LCP to deliver ATP pulses.

If the intrinsic heart rate rises to and/or above an upper heart rate threshold and into a "Post Shock Zone", the processing module 110 may instruct the pulse generator module 104 to temporarily set the energy level of pacing pulses, if delivered, to an enhanced energy level above the capture pacing energy level for a period of time. After the period of time expires, the energy level of pacing pulses may be returned to the capture energy level. During the period of time, it is contemplated that the pacing pulses, if delivered, may be demand-pacing pacing pulses, post-shock pacing pulses, and/or anti-tachyarrhythmia-pacing (ATP) pulses, depending on what is deemed appropriate therapy by the processing module 110 at any given time.

The upper heart rate threshold may be a threshold that may be fixed or programmable. The upper heart rate threshold may be set at a rate that is above a safe heart rate of the patient, such that if the patient's heart rate rises above the upper heart rate threshold, the patient may be experiencing tachycardia and even cardiac fibrillation. Anticipating that a shock may be delivered to the heart via another medical device (e.g. an Implantable Cardioverter Defibrillator), the processing module 110 may instruct the pulse generator module 104 to temporarily set the energy level of pacing pulses, if delivered, to an enhanced energy level above the capture pacing energy level for a period of time. The period of time may be 30 seconds, 1 minute, 3 minutes, 5 minutes, 10 minutes, 20 minutes, 30 minutes, 1 hour, 1 day, or any other suitable time period. While this may consume extra power during this period of time by delivering some pacing pulses at the enhanced energy level, the pulses will be more appropriate for post-shock pacing should a shock be delivered to the heart by another medical device. Note, this allows the LCP 100 to autonomously set the pacing pulses to an enhanced energy level for post shock-pacing without having to first detect a high energy shock pulse or receive a communication from another medical device notifying the LCP that a shock will be delivered. Whether a shock pulse is actually delivered or not, the processing module 110 may instruct the pulse generator module 104 to temporarily set the energy level of pacing pulses, if delivered, to an enhanced energy level until the end of the time period, and then return the energy level back to the capture energy level. In some cases, the period of time may be reset each time the measured heart rate is above the upper heart rate threshold. When so provided, the pulse generator module 104 keep the energy level at the enhanced energy level until the heart rate remains below the upper heart rate threshold for at least the period of time.

In some case, the processing module 110 may detect when the sensed heart rate falls at a rate that is above a threshold rate and/or falls below a floor heart rate. When the heart rate falls at a rate that is outside the bounds of normal physiology, or falls below a heart rate that is below what is necessary to sustain life, it may be assumed that the heart has been shocked by an ICD or the like. In response, the processing module may instruct the pulse generator module 104 to deliver pacing pulses (e.g. post shock pacing pulses) at the enhanced energy level until the end of the time period, and then return the energy level back to the capture energy level. This may be an alternative trigger for temporarily delivering pacing pulses at the enhanced energy level for a period of time.

In certain embodiments, the LCP 100 may include the communication module 102. In some cases, the communication module 102 may be configured to communicate with devices such as remote sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
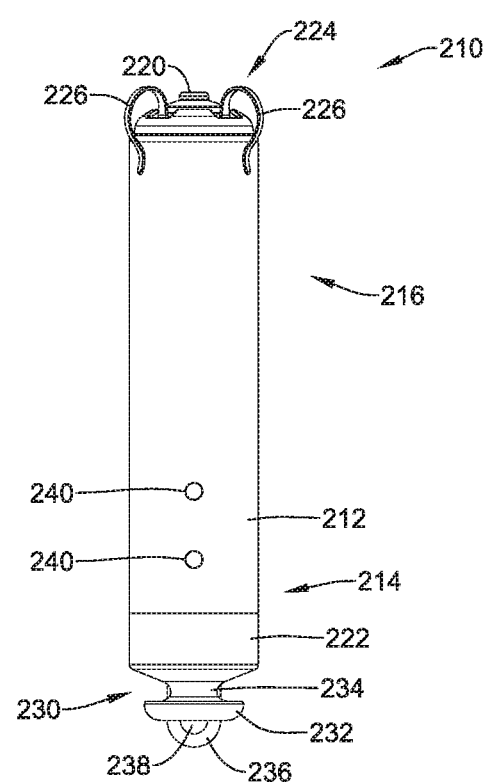
FIG. 2 is a side view of an illustrative implantable LCP.

FIG. 2 is a side view of an illustrative implantable leadless cardiac pacemaker (LCP) 210. The LCP 210 may be similar in form and function to the LCP 100 described above. The LCP 210 may include the control module having any of the modules and/or structural features described above with respect to the LCP 100 described above. The LCP 210 may include a shell or housing 212 having a proximal end 214 and a distal end 216. The illustrative LCP 210 includes a first electrode 220 secured relative to the housing 212 and positioned adjacent to the distal end 216 of the housing 212 and a second electrode 222 secured relative to the housing 212 and positioned adjacent to the proximal end 214 of the housing 212. The electrodes 220, 222 may be sensing and/or pacing electrodes to provide electro-therapy and/or sensing capabilities. The first electrode 220 may be capable of being positioned against or may otherwise contact the cardiac tissue of the heart while the second electrode 222 may be spaced away from the first electrode 220. The first and/or second electrodes 220, 222 may be exposed to the environment outside the housing 212 (e.g. to blood and/or tissue).

In some cases, the LCP 210 may include a pulse generator (e.g., electrical circuitry) and an energy storage module (e.g., a battery, supercapacitor and/or other power source) within the housing 212 to provide electrical signals to the electrodes 220, 222 to control the pacing/sensing electrodes 220, 222. While not explicitly shown, the LCP 210 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 212. Electrical connections between the pulse generator and the electrodes 220, 222 may allow electrical stimulation to heart tissue and/or sense a physiological parameter.

In the example shown, the LCP 210 includes a fixation mechanism 224 proximate the distal end 216 of the housing 212. The fixation mechanism 224 is configured to attach the LCP 210 to a wall of the heart, or otherwise anchor the LCP 210 to the anatomy of the patient. In some instances, the fixation mechanism 224 may include one or more, or a plurality of hooks or tines 226 anchored into the cardiac tissue of the heart to attach the LCP 210 to a tissue wall. In other instances, the fixation mechanism 224 may include one or more, or a plurality of passive tines, configured to entangle with trabeculae within the chamber of the heart and/or a helical fixation anchor configured to be screwed into a tissue wall to anchor the LCP 210 to the heart. These are just examples.

The LCP 210 may further include a docking member 230 proximate the proximal end 214 of the housing 212. The docking member 230 may be configured to facilitate delivery and/or retrieval of the LCP 210. For example, the docking member 230 may extend from the proximal end 214 of the housing 212 along a longitudinal axis of the housing 212. The docking member 230 may include a head portion 232 and a neck portion 234 extending between the housing 212 and the head portion 232. The head portion 232 may be an enlarged portion relative to the neck portion 234. For example, the head portion 232 may have a radial dimension from the longitudinal axis of the LCP 210 that is greater than a radial dimension of the neck portion 234 from the longitudinal axis of the LCP 210. In some cases, the docking member 230 may further include a tether retention structure 236 extending from or recessed within the head portion 232. The tether retention structure 236 may define an opening 238 configured to receive a tether or other anchoring mechanism therethrough. While the retention structure 236 is shown as having a generally "U-shaped" configuration, the retention structure 236 may take any shape that provides an enclosed perimeter surrounding the opening 238 such that a tether may be securably and releasably passed (e.g. looped) through the opening 238. In some cases, the retention structure 236 may extend though the head portion 232, along the neck portion 234, and to or into the proximal end 214 of the housing 212. The docking member 230 may be configured to facilitate delivery of the LCP 210 to the intracardiac site and/or retrieval of the LCP 210 from the intracardiac site. While this describes one example docking member 230, it is contemplated that the docking member 230, when provided, can have any suitable configuration.

It is contemplated that the LCP 210 may include one or more pressure sensors 240 coupled to or formed within the housing 212 such that the pressure sensor(s) is exposed to the environment outside the housing 212 to measure blood pressure within the heart. For example, if the LCP 210 is placed in the left ventricle, the pressure sensor(s) 240 may measure the pressure within the left ventricle. If the LCP 210 is placed in another portion of the heart (such as one of the atriums or the right ventricle), the pressures sensor(s) may measure the pressure within that portion of the heart. The pressure sensor(s) 240 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 240 may be part of a mechanical sensing module described herein. It is contemplated that the pressure measurements obtained from the pressures sensor(s) 240 may be used to generate a pressure curve over cardiac cycles. The pressure readings may be taken in combination with impedance measurements (e.g. the impedance between electrodes 220 and 222) to generate a pressure-impedance loop for one or more cardiac cycles as will be described in more detail below. The impedance may be a surrogate for chamber volume, and thus the pressure-impedance loop may be representative for a pressure-volume loop for the heart.

In some embodiments, the LCP 210 may be configured to measure impedance between the electrodes 220, 222. More generally, the impedance may be measured between other electrode pairs, such as the additional electrodes 114' described above. In some cases, the impedance may be measured between two spaced LCP's, such as two LCP's implanted within the same chamber (e.g. LV) of the heart, or two LCP's implanted in different chambers of the heart (e.g. RV and LV). The processing module of the LCP 210 and/or external support devices may derive a measure of cardiac volume from intracardiac impedance measurements made between the electrodes 220, 222 (or other electrodes). Primarily due to the difference in the resistivity of blood and the resistivity of the cardiac tissue of the heart, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 210 may be provided with energy delivery circuitry operatively coupled to the first electrode 220 and the second electrode 222 for causing a current to flow between the first electrode 220 and the second electrode 222 in order to determine the impedance between the two electrodes 220, 222 (or other electrode pair). It is contemplated that the energy delivery circuitry may also be configured to deliver pacing pulses via the first and/or second electrodes 220, 222. The LCP 210 may further include detection circuitry operatively coupled to the first electrode 220 and the second electrode 222 for detecting an electrical signal received between the first electrode 220 and the second electrode 222. In some instances, the detection circuitry may be configured to detect cardiac signals received between the first electrode 220 and the second electrode 222.

When the energy delivery circuitry delivers a current between the first electrode 220 and the second electrode 222, the detection circuitry may measure a resulting voltage between the first electrode 220 and the second electrode 222 (or between a third and fourth electrode separate from the first electrode 220 and the second electrode 222, not shown) to determine the impedance. When the energy delivery circuitry delivers a voltage between the first electrode 220 and the second electrode 222, the detection circuitry may measure a resulting current between the first electrode 220 and the second electrode 222 (or between a third and fourth electrode separate from the first electrode 220 and the second electrode 222) to determine the impedance.

From these and other measurements, heart rate, respiration, stroke volume, contractility, and other physiological parameters can be derived.

Figure 3:
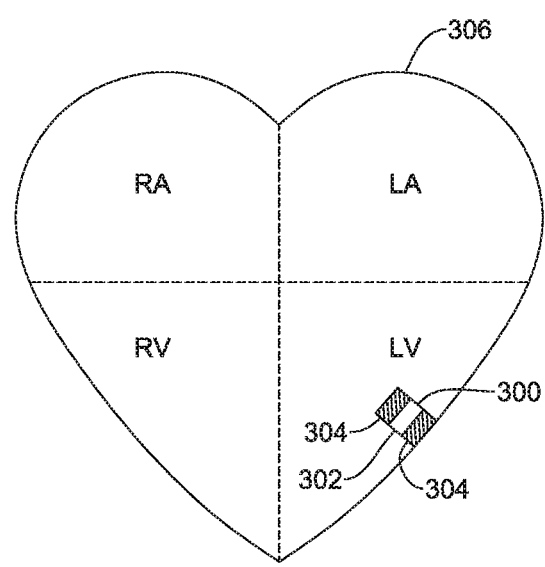
FIG. 3 is a schematic diagram of an LCP implanted in a chamber of a patient's heart, in accordance with an example of the disclosure.

FIG. 3 shows an illustrative LCP 300 implanted in a heart 306. In FIG. 3, the LCP 300 is shown fixed to the interior of the left ventricle (LV) of the heart 306. In some cases, the LCP 300 may be in the right ventricle, right atrium, left ventricle or left atrium of the heart, as desired. In some cases, more than one LCP 300 may be implanted. For example, one LCP 300 may be implanted in the right ventricle and another may be implanted in the right atrium. In another example, one LCP 300 may be implanted in the right ventricle and another may be implanted in the left ventricle. In yet another example, one LCP 300 may be implanted in each of the chambers of the heart.

According to various embodiments, the LCP 300 may include a housing 302 having electrodes 304 for sensing electrical signals emanating from outside of the housing 302. The electrodes 304 may be configured to provide sensed cardiac signals to a control module disposed with the housing 302. The control module may then determine a heart rate of the heart 306 based on the cardiac signals and instruct a pulse generator to deliver pacing pulses to the heart 306 via the electrodes 304.

According to various embodiments, the control module may cause the LCP 300 to deliver demand pacing. In demand pacing, the LCP 300 may monitor the heart rate and send an electrical pacing pulse or electrical pacing pulses to the heart 306 if the intrinsic heart rate is too slow and/or if beats are being missed. Said another way, the LCP 300 may pace the heart at a lower heart rate threshold when the intrinsic heart rate falls below the lower heart rate threshold, and missed intrinsic beats may be paced. In one example, in demand pacing, when the control module receives cardiac signals from the electrodes 304, the control module may analyze the cardiac signals and determine a measure of heart rate. In some cases, the determined measure of the heart rate may be an average heart rate of more than one or a set of previously recorded heart beats. In certain embodiments, the control module may then compare the measure of the heart rate to the lower heart rate threshold (e.g. a fixed heart rate threshold or a demand heart rate threshold). In some cases, the control module may be programmed to keep the measure of the heart rate from falling below the lower heart rate threshold. As a result, if the intrinsic heart rate falls below the lower heart rate threshold, such as 60 bpm, the control module instructs the pulse generator to deliver electrical pacing pulses at the lower heart rate threshold and at a first energy level using the electrodes 304. The lower heart rate threshold may be any suitable heart rate, such as 70 bpm, 60 bpm, 50 bpm, 45 bpm, 40 bpm, etc. It is contemplated that the lower heart rate threshold may be a fixed heart rate such as a lower rate limit, or may be a dynamic heart rate that is dependent on the activity level of the patient.

In various embodiments, the desired energy level of the pacing pulses may dictate the amplitude and/or the pulse width of the electrical pacing pulses that are delivered to the heart. In certain embodiments, the first energy level may deliver pacing pulses each having an electrical pulse width of 1 ms and an amplitude of 5.0 V. In some embodiments, the first energy level may deliver pacing pulses each having an electrical pulse width of 0.5 ms and an amplitude of 4.0 V. In further embodiments, the first energy level may deliver pacing pulses each having an electrical pulse width of 0.25 ms and an amplitude of 3.0 V amplitude. These are just examples and other amplitudes and pulse widths may be designated for the first energy level at which the demand pacemaker delivers electrical pulses. In some instances, the first energy level may be set based on the results of a capture threshold test. For example, the first energy level may be set at the capture threshold plus a capture threshold margin. In some instances, changing the energy level may only change the amplitude and keep the pulse width the same, or change the pulse width and keep the amplitude the same, or change both the amplitude and pulse width.

In some cases, while the pulse generator delivers pacing pulses at the first energy level, the control module may continue to use the electrodes 304 to sense the cardiac signals and determine and monitor the heart rate. In some cases, the control module may continue to instruct the pulse generator to deliver the electrical pacing pulses until the intrinsic rate is above the lower heart rate threshold.

In various embodiments, the control module may cause the LCP 300 to deliver ATP therapy pulses. In ATP therapy, the LCP 300 may monitor the heart rate and send an electrical pacing pulse or electrical pacing pulses to the heart 306 if the intrinsic heart rate is above a normal heart rate. In one example, in ATP therapy, when the control module receives cardiac signals from the electrodes 304, the control module may analyze the cardiac signals and determine a measure of heart rate. In some cases, the determined measure of the heart rate may be an average heart rate of more than one or a set of previously recorded heart beats. In certain embodiments, the control module may then compare the measure of the heart rate to the higher heart rate threshold (e.g. a fixed heart rate threshold or a normal heart rate threshold). In some cases, the control module may be programmed to attempt to keep the measure of the heart rate from rising above the higher heart rate threshold by delivering ATP therapy if appropriate. As a result, if the intrinsic heart rate rises above the higher heart rate threshold, such as 140 bpm, the control module may instruct the pulse generator to deliver ATP therapy pulses at the first energy level using the electrodes 304. The higher heart rate threshold may be any suitable heart rate, such as 155 bpm, 150 bpm, 145 bpm, 135 bpm, etc. It is contemplated that the higher heart rate threshold may be a fixed heart rate such as a higher rate limit, or may be a dynamic heart rate that is dependent on the activity level of the patient.

In some cases, while the pulse generator delivers ATP pulses at the first energy level, the control module may continue to use the electrodes 304 to sense the cardiac signals and determine and monitor the heart rate. In some cases, the control module may continue to instruct the pulse generator to deliver the ATP pulses until the intrinsic rate falls below the higher heart rate threshold or until a predetermined period has passed.

While monitoring the measure of the heart rate, the control module may detect when the heart rate rises above an upper heart rate threshold. If the heart rate is below the upper heart rate threshold, the pacing pulses may be delivered at the first energy level as discussed above. However, if the heart rate rises above the upper heart rate threshold, the control module may cause pacing pulses to be temporarily delivered at an enhanced energy level above the first energy level for a period of time, and after the period of time, the pacing pulses may again be delivered at the first energy level. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what is deemed appropriate therapy at any given time.

The upper heart rate threshold may be a threshold that may be fixed or programmable. The upper heart rate threshold may be set at a rate that is above a safe heart rate of the patient, such that if the patient's heart rate rises above the upper heart rate threshold, the patient may be experienced tachycardia and even cardiac fibrillation. Anticipating that a shock may be delivered to the heart via another medical device (e.g. an Implantable Cardioverter Defibrillator), the control module of the LCP 300 may instruct a pulse generator module of the LCP 300 to temporarily deliver pacing pulses at the enhanced energy level above the first energy level for a period of time. The period of time may be 30 seconds, 1 minute, 3 minutes, 5 minutes, 10 minutes, 20 minutes, 30 minutes, 1 hour, 1 day, or any other suitable time period. While this may consume extra power during this period of time by delivering pacing pulses at the enhanced energy level rather than the lower first energy level, the pacing pulses will be delivering pacing pulses that are more appropriate for post-shock pacing pulses should a shock be delivered to the heart by another medical device. Note, this allows the LCP 300 to autonomously set the pacing pulses to an enhanced energy level for post shock-pacing without having to have circuitry to detect a high energy shock pulse or receive a communication from another medical device notifying the LCP 300 that a shock will be delivered. Whether a shock pulse is actually delivered or not, the control module may instruct the pulse generator module to temporarily deliver pacing pulses at the enhanced energy level until the end of the time period, and then return to delivering pacing pulses at the first energy level. In some cases, the period of time may be reset each time the measured heart rate is above the upper heart rate threshold. When so provided, the control module of the LCP 300 may deliver pacing pulses at the enhanced energy level until the heart rate remains below the upper heart rate threshold for the period of time. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what the control module deems appropriate therapy at any given time.

In some case, the control module may detect when the sensed heart rate falls at a rate that is above a threshold and/or falls below a floor heart rate. When the heart rate falls at a rate that is outside the bounds of normal physiology, or falls below a heart rate that is below what is necessary to sustain life, the control module may assume that the heart has just been shocked by an ICD. In response, the control module may instruct the pulse generator module of the LCP 300 to temporarily deliver pacing pulses at the enhanced energy level until the end of a time period, and then return to delivering pacing pulses at the first energy level. This may be an alternative trigger for temporarily delivering pacing pulses at the enhanced energy level for a period of time.

In certain embodiments, the enhanced energy level may have an electrical pulse width of 1.5 ms and a 5.0 V amplitude. In some embodiments, the enhanced energy level may have an electrical pulse width of 1.5 ms and a 7.0 V amplitude. In some embodiments, the enhance energy level may have an electrical pulse width of 2 ms and an 8.0 V amplitude. In further embodiments, the enhanced energy level may have an electrical pulse width of 2.5 ms and an 8.5 V amplitude. These are just examples and other amplitudes and pulse widths may be designated for the enhanced energy level. In some cases, the enhanced energy level may have an amplitude that is a maximum voltage, and the pulse width is the same or larger than that used for the first energy level. In some cases, when changing between the first energy level and the enhanced energy level, the control module may only change the pulse amplitude of the electrical pacing pulses and leave the pulse widths the same, only change the pulse widths and leave the pulse amplitudes the same, or both change pulse amplitude and pulse width.

Figure 4:
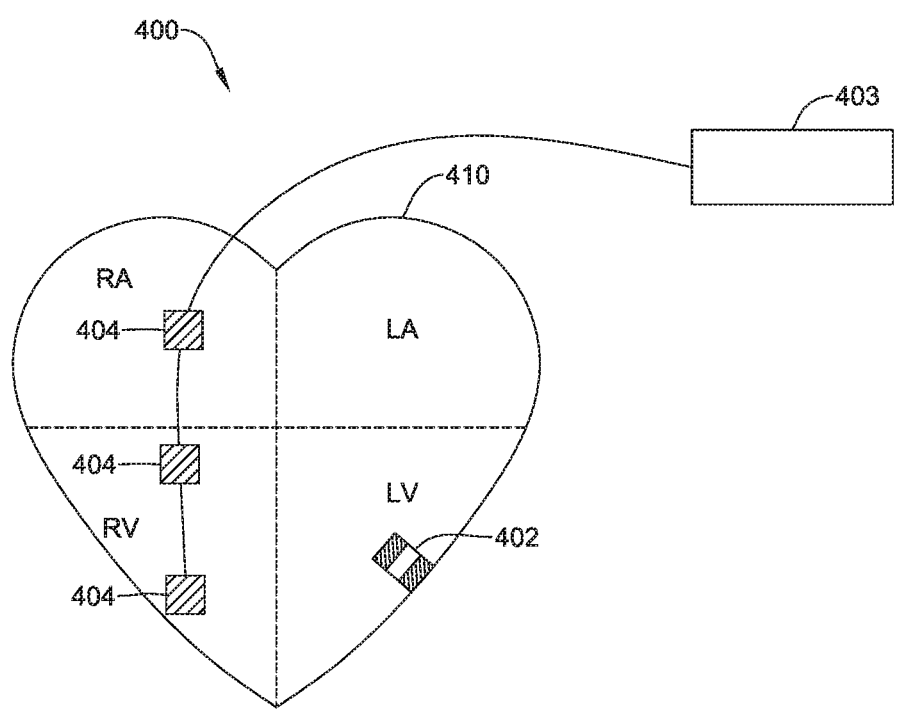
FIG. 4 is a schematic diagram of a co-implanted transvenous implantable cardioverter-defibrillator (T-ICD) and LCP, in accordance with an example of the disclosure.

FIG. 4 is a schematic diagram of a co-implanted transvenous implantable cardioverter-defibrillator (T-ICD) 400 and LCP 402, in accordance with an example of the disclosure. In FIG. 4, the ICD 400 may include a pulse generator 403 coupled to a lead 406 having one or more electrodes 404. In some cases, the electrodes 404 may be positioned in the heart 410. The location of the pulse generator 403, the lead 406, and electrodes 404 are just exemplary. In some cases, the pulse generator 403, the lead 406 and/or electrodes 404 may be disposed in different chambers of the heart 410, or the pulse generator 403 may include additional leads and/or electrodes that are disposed within or adjacent to heart 410. According to various embodiments, the ICD 400 may be configured to deliver a shock to the heart 410.

The LCP 402 may operate similar to the LCPs 100, 210 and 300 discussed above. The LCP 402 may be configured to deliver demand pacing. In demand pacing, the LCP 402 may monitor the heart rate and send an electrical pacing pulse or electrical pacing pulses to the heart 410 if the intrinsic heart rate is too slow and/or if beats are being missed. Said another way, the LCP 402 may pace the heart at a lower heart rate threshold when the intrinsic heart rate falls below the lower heart rate threshold, and missed intrinsic beats may be paced. In one example, in demand pacing, when the LCP 402 receives cardiac signals from its electrodes, the LCP 402 may analyze the cardiac signals and determine a measure of heart rate. In some cases, the determined measure of the heart rate may be an average heart rate of more than one or a set of previously recorded heart beats. In certain embodiments, the LCP 402 may then compare the measure of the heart rate to the lower heart rate threshold (e.g. a fixed heart rate threshold or a demand heart rate threshold). In some cases, the LCP 402 may be programmed to keep the measure of the heart rate from falling below the lower heart rate threshold. As a result, if the intrinsic heart rate falls below the lower heart rate threshold, such as 60 bpm, the LCP 402 delivers electrical pacing pulses at the lower heart rate threshold and at a first energy level.

While monitoring the measure of the heart rate, the control module may detect when the heart rate rises above a higher heart rate threshold. If the heart rate rises above the higher heart rate threshold, the LCP 402 may be configured to deliver ATP therapy. In ATP therapy, the LCP 402 may monitor the heart rate and send an electrical pacing pulse or electrical pacing pulses to the heart 410 if the intrinsic heart rate is too high. In one example, in ATP therapy, when the LCP 402 receives cardiac signals from its electrodes, the LCP 402 may analyze the cardiac signals and determine a measure of heart rate. In some cases, the determined measure of the heart rate may be an average heart rate of more than one or a set of previously recorded heart beats. In certain embodiments, the LCP 402 may then compare the measure of the heart rate to the higher heart rate threshold (e.g. a fixed heart rate threshold or a demand heart rate threshold). In some cases, the LCP 402 may attempt to keep the measure of the heart rate from rising above the higher heart rate threshold by applying ATP therapy if appropriate. As a result, if the intrinsic heart rate rises above the higher heart rate threshold, such as 140 bpm, the LCP 402 may delivers ATP therapy at the first energy level.

While monitoring the measure of the heart rate, the control module may detect when the heart rate rises above an upper heart rate threshold. If the heart rate is below the upper heart rate threshold, the pacing pulses may be delivered at the first energy level as discussed above. However, if the heart rate rises above the upper heart rate threshold, the LCP 402 may cause pacing pulses to be temporarily delivered at an enhanced energy level above the first energy level for a period of time, and after the period of time, the pacing pulses may again be delivered at the first energy level. During the period of time, it is contemplated that the pacing pulses delivered at the enhanced energy level may comprise demand-pacing pacing pulses, post-shock pacing pulses, and/or anti-tachyarrhythmia-pacing (ATP) pulses, depending on what is deemed appropriate therapy at any given time.

The upper heart rate threshold may be a threshold that may be fixed or programmable. The upper heart rate threshold may be set at a rate that is above a safe heart rate of the patient, such that if the patient's heart rate rises above the upper heart rate threshold, the patient may be experiencing tachycardia and even cardiac fibrillation. Anticipating that a shock may be delivered to the heart via the ICD 400, the LCP 402 may temporarily deliver pacing pulses at the enhanced energy level above the first energy level for a period of time. While this may consume extra power during this period of time by delivering pacing pulses at the enhanced energy level rather than the lower first energy level, the pacing pulses will be delivering pacing pulses that are more appropriate for post-shock pacing pulses should a shock be delivered to the heart 410 by the ICD 400. Note, this allows the LCP 402 to autonomously set the pacing pulses to an enhanced energy level for post shock-pacing without having to have circuitry to detect a high energy shock pulse or receive a communication from ICD 400 notifying the LCP 402 that a shock will be delivered. Whether a shock pulse is actually delivered or not by the ICD 400 during the time period, the LCP 402 may temporarily deliver pacing pulses at the enhanced energy level until the end of the time period, and then return to delivering pacing pulses at the first energy level. In some cases, the period of time may be reset each time the measured heart rate is above the upper heart rate threshold. When so provided, the LCP 402 may deliver pacing pulses at the enhanced energy level until the heart rate remains below the upper heart rate threshold for the period of time. During the period of time, it is contemplated that the pacing pulses delivered at the enhance energy level may comprise demand-pacing pacing pulses, post-shock pacing pulses, and/or anti-tachyarrhythmia-pacing (ATP) pulses, depending on what the control module deems appropriate therapy at any given time.

In some case, the LCP 402 may detect when the sensed heart rate falls at a rate that is above a threshold and/or falls below a floor heart rate. When the heart rate falls at a rate that is outside the bounds of normal physiology, or falls below a heart rate that is below what is necessary to sustain life, the LCP 402 may assume that the heart has just been shocked by the ICD 400. In response, the LCP 402 may temporarily deliver pacing pulses at the enhanced energy level until the end of a time period, and then return to delivering pacing pulses at the first energy level. This may be an alternative trigger for temporarily delivering pacing pulses at the enhanced energy level for a period of time.

In some cases, the ICD 400 may monitor the heart 410 and determine if the heart 410 is experiencing cardiac fibrillation or other condition that necessitates delivery of a high energy shock therapy. This may include the detection of rapid, irregular, and/or inefficient heart contractions. In some cases, before delivering the shock therapy, the ICD 400 may communicate an ATP command to the LCP 402 to deliver anti-tachyarrhythmia-pacing (ATP) pulses to the heart 410. In some cases, anti-tachyarrhythmia-pacing (ATP) pulses may cause the heart 410 to return to a normal rhythm without delivering a high energy shock. The LCP 402 may receive the ATP command and deliver the requested ATP pulses. In some cases, the energy level of the ATP pulses may be at an enhanced energy level. In some cases, the LCP 402 may have already detected a high heart rate and already adjusted the energy level of the delivered pulses (for a period of time) to the enhanced energy level. In other cases, the LCP 402 may adjust the energy level of the delivered pulses in response to receiving the ATP command from the ICD 400.

Figure 5:
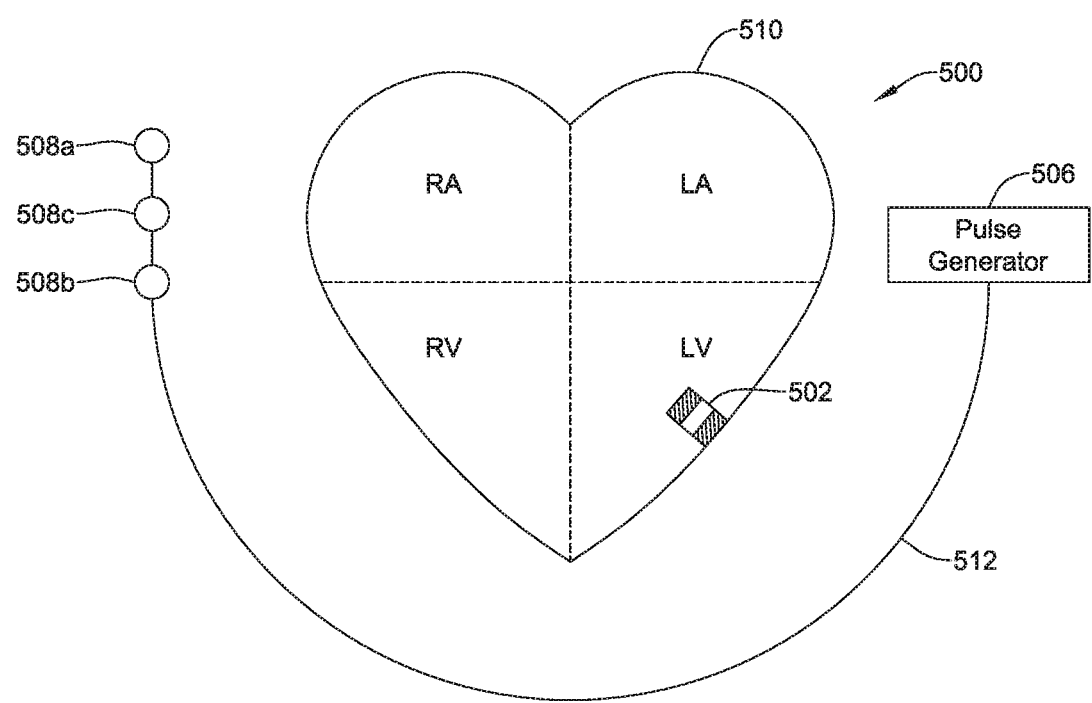
FIG. 5 is a schematic diagram of a co-implanted subcutaneous or substernum implantable cardioverter-defibrillator (S-ICD) and LCP, in accordance with an example of the disclosure.

FIG. 5 is a schematic diagram of a co-implanted subcutaneous or substernum implantable cardioverter-defibrillator (S-ICD) 500 and LCP 502, in accordance with an example of the disclosure. In FIG. 5, the LCP 502 is shown fixed to the interior of the left ventricle of the heart 510. A subcutaneous or substernum implantable cardioverter-defibrillator (S-ICD) 500 is shown implanted near the heart. The illustrative subcutaneous or substernum implantable cardioverter-defibrillator (S-ICD) 500 includes a pulse generator 506 that may be implanted subcutaneous, and a lead 512 with one or more electrodes 508a-508c that extends subcutaneous or substernum (e.g. just interior of the sternum) adjacent but outside of the heart 510. The pulse generator 506 is configured to deliver a shock to the heart via one or more of the electrodes 508a-508c. The LCP 502 may operate in a similar manner to that described above with respect to FIG. 4, but with the subcutaneous or substernum implantable cardioverter-defibrillator (S-ICD) 500 configured to deliver the shock therapy rather than the transvenous ICD 400.

FIGS. 6A-6F are timing diagrams showing illustrative operations of an LCP under various operating conditions. As shown in FIGS. 6A-6F, traces for an intrinsic heart rate 602, a demand heart rate threshold 604, an ATP threshold 624, an upper limit threshold 606, a life sustaining threshold 608, an active energy level 610, and a pacing therapy 612. According to various embodiments, an LCP may monitor the intrinsic heart rate 602, and may deliver electrical pacing pulses to the heart when the intrinsic heart rate 602 is too low, when there is a sudden drop in the heart rate, and/or when intrinsic heart beats are being skipped or missed.

Figure 6A:
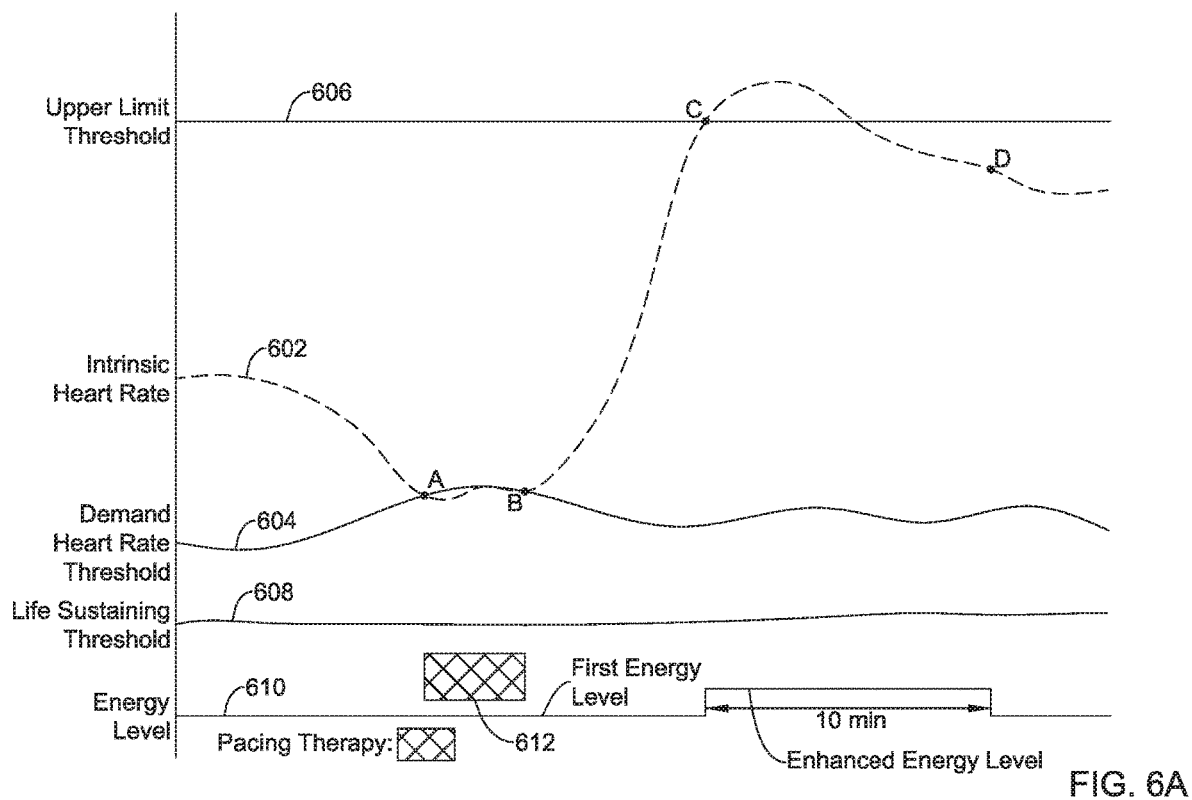
FIGS. 6A-6G are timing diagrams showing illustrative operations of an LCP under various operating conditions.

Turning specifically to FIG. 6A, the intrinsic heart rate 602 is initially above the demand heart rate threshold 604 and below the upper limit threshold 606. In some cases, the intrinsic heart rate 602 may be an average heart rate of more than one or a set of previously recorded heart beats. The demand heart rate threshold 604 that may vary according to fluctuations in hemodynamic demand, as detected by changes in patient activity, respiration, blood temperature, body tissue temperature, etc. Although not shown in FIGS. 6A-6f, it is contemplated that the demand heart rate threshold 604 may be a fixed heart rate threshold (e.g., 70 bpm, 60 bpm, 50 bpm, 40 bpm, etc.).

The upper limit threshold 606 may be a threshold that may be variable (e.g. depend on fluctuations in hemodynamic demand), fixed and/or programmable. In FIG. 6A, the upper limit threshold 606 is a fixed heart rate threshold. In various embodiments, the upper limit threshold 606 may be set at a rate that is above a safe heart rate for the patient, such that if the patient's heart rate rises above the upper limit threshold 606, the patient may be experiencing tachycardia and even cardiac fibrillation. Initially, the intrinsic heart rate 602 is below the upper limit threshold 606, and because the intrinsic heart rate 602 is not falling at a rate that is above a maximum decrease threshold, the active energy level 610 at which the LCP would delivers pacing pulses may be set at a first energy level.

As shown in FIG. 6A, at point A, the intrinsic heart rate 602 has fallen below the demand heart rate threshold 604. In some cases, the LCP may pace the heart when the intrinsic heart rate falls below the demand heart rate threshold 604. As shown in FIG. 6A, pacing therapy 612 is delivered at the first energy level until point B, where the intrinsic heart rate 602 rises above the demand heart rate threshold 604. This is an example of demand pacing, which helps ensure that the heart rate of a patient does not fall below a lower heart rate threshold such as the demand heart rate threshold 604. When performing demand pacing, the LCP may pace the heart at the lower heart rate threshold (e.g. demand heart rate threshold 604) when the intrinsic heart rate falls below the lower heart rate threshold (e.g. demand heart rate threshold 604).

After point B, the active energy level 610 is still set at the first energy level as the intrinsic heart rate 602 continues to rise. At point C, the intrinsic heart rate 602 has reached the upper limit threshold 606, at which point the LCP increases the active energy level 610 to an enhanced energy level. When demand pacing, and as shown in FIG. 6A, the LCP may not deliver pacing therapy 612 to the heart at the enhanced energy level while the intrinsic heart rate 602 remains above the demand heart rate threshold 604. In certain embodiments, the active energy level 610 may be increased to the enhanced energy level for a period time. In FIG. 6A, the period of time has been set for 10 minutes. During the 10 minute time period, it is contemplated that pacing therapy 612 will be delivered with pacing pulses having the enhanced energy level. The pacing therapy 612 may be demand-pacing pacing pulses, post-shock pacing pulses, anti-tachyarrhythmia-pacing (ATP) pulses and/or any other suitable pacing therapy depending on what is deemed appropriate pacing therapy at any given time. As shown in FIG. 6A, the intrinsic heart rate 602 falls back under the upper limit threshold 606 before the 10 minute time period has expired. The LCP then decreases the active energy level 610 back to the first energy level at point D, when the 10 minute time period has expired.

Figure 6B:
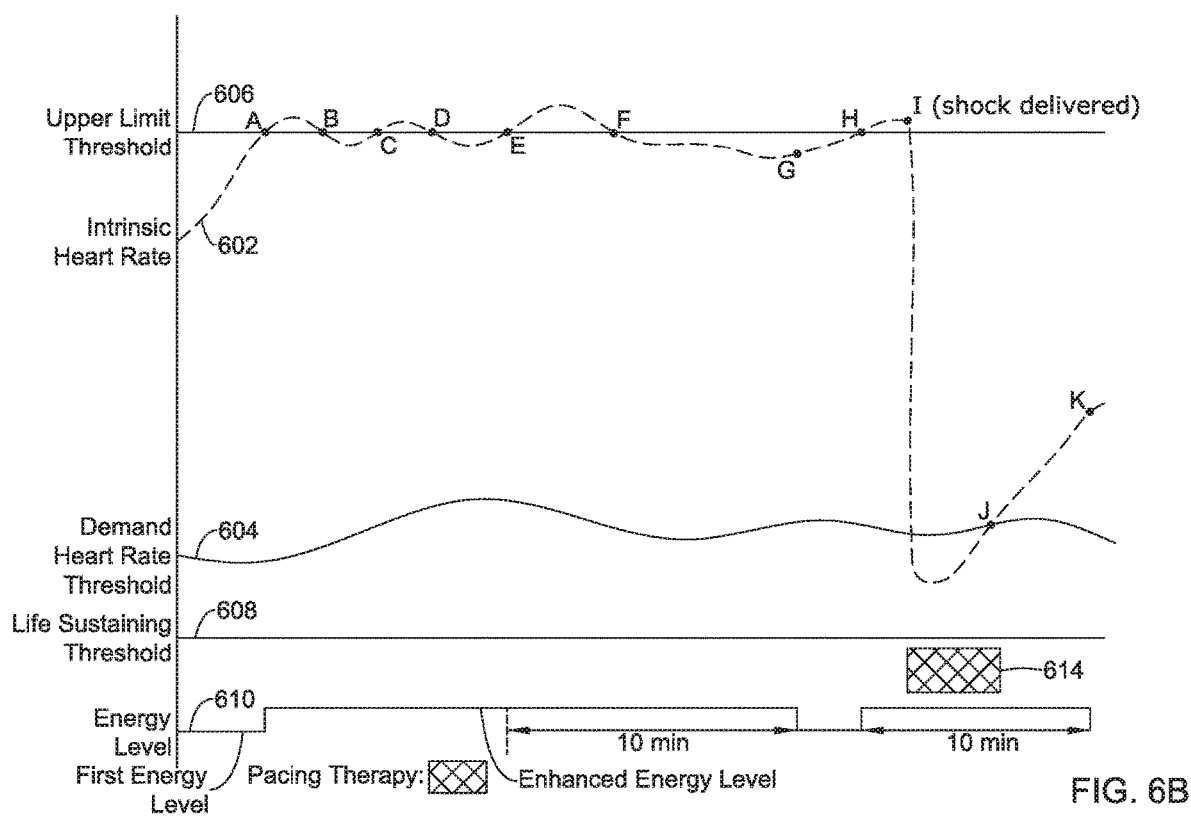

Turning now to FIG. 6B, the intrinsic heart rate 602 is initially below the upper limit threshold 606 and the intrinsic heart rate 602 is not falling at a rate that is above a maximum decrease threshold. As a result, the LCP may set the active energy level 610 at which the LCP would deliver pacing pulses to the first energy level. The intrinsic heart rate 602 then rises and reaches the upper limit threshold 606 at point A. In response, the LCP may set the active energy level 610 to the enhanced energy level for a time period such as 10 minutes. At point B, the intrinsic heart rate 602 falls back under the upper limit threshold 606 before the 10 minutes has expired, but the active energy level 610 may remain at the enhanced energy level. At point C, the intrinsic heart rate 602 once again rises above the upper limit threshold 606. In some cases, as depicted in FIG. 6B, if the intrinsic heart rate 602 rises above the upper limit threshold 606 before the 10 minute time period has expired from the previous time (point A) that the intrinsic heart rate 602 went above the upper limit threshold 606, the time period may be reset back to zero such that the active energy level 610 may remain at the enhanced energy level until 10 minutes after point C. At point D, the intrinsic heart rate 602 falls back under the upper limit threshold 606 before the reset 10 minute timer has expired, and the active energy level 610 may remain at the enhanced energy level. At point E, the intrinsic heart rate 602 again rises above the upper limit threshold 606 for a third time, and the 10 minute time period is once again reset. At point F, the intrinsic heart rate 602 falls back under the upper limit threshold 606 before the 10 minutes has expired. The active energy level 610 remains at the enhanced energy level until point G, when the 10 minute time period finally expires. In this example, the active energy level 610 remains at the enhanced energy level for 10 minutes following the last time the intrinsic heart rate 602 rises in a positive direction above the upper limit threshold 606.

At point H, the intrinsic heart rate 602 again rises to the upper limit threshold 606 and the active energy level 610 may be again increased from the first energy level to the enhanced energy level for a 10 minute time period, which might be extended as described above. At point I, the intrinsic heart rate 602 has started falling at a rate that is above the maximum decrease threshold. This may indicate that an ICD may have delivered a shock to the patient's heart. As a result, the LCP may be configured to deliver post shock pacing therapy 614 at the enhanced energy level. As shown in FIG. 6B, the post shock pacing therapy 614 may be delivered until point J, where the intrinsic heart rate 602 rises above the demand heart rate threshold 604. In some cases, the post shock pacing therapy 614 may be delivered for a predetermined period of time or until the intrinsic heart rate 602 has stabilized. Even though the post shock pacing therapy 614 is no longer being delivered after point J, in this example, the active energy level 610 may not decrease back to the first energy level until point K, when the 10 minute window has expired.

Figure 6C:
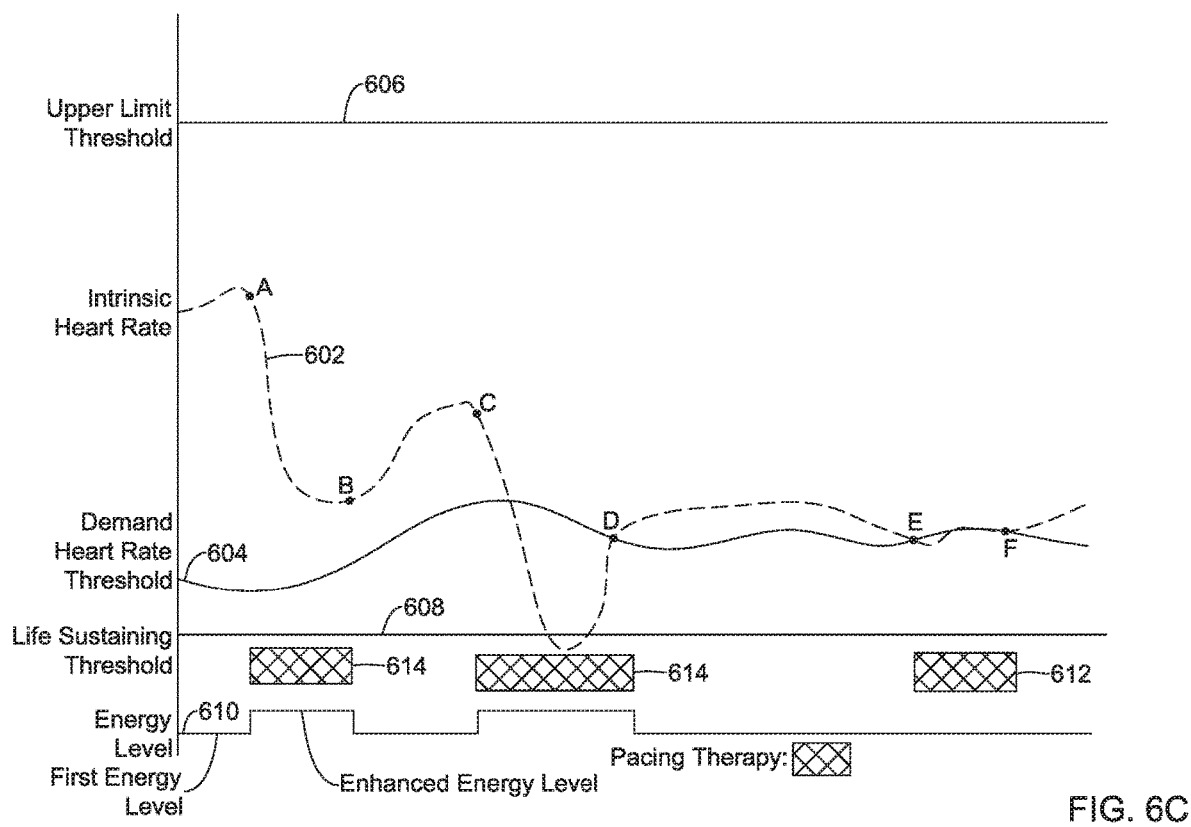

Turning now to FIG. 6C, the initial intrinsic heart rate 602 is below the upper limit threshold 606 and the intrinsic heart rate 602 is not falling at a rate that is above the maximum decrease threshold. As a result, the active energy level 610 may be set at a first energy level at which the LCP delivers pacing pulses. At point A, the intrinsic heart rate 602 has started falling at a rate that is above the maximum decrease threshold. In response, in this example, the active energy level 610 may instantaneously be increased to the enhanced energy level and a post shock pacing therapy 614 may be delivered using pulses at the enhanced energy level. As shown in FIG. 6C, the post shock pacing therapy 614 may be delivered until point B, where the intrinsic heart rate 602 has stabilized (or after a predetermined period of time). In this example, because the intrinsic heart rate 602 did not rise above the upper limit threshold 606 before it started falling at a rate above the maximum decrease threshold, the active energy level 610 may be decreased back to the first energy level once the intrinsic heart rate 602 has stabilized (or after a predetermined period of time). However, it is contemplated that the active energy level 610 may remain at the enhanced energy level for a period of time.

At point C, the intrinsic heart rate 602 once again begins falling at a rate that is above the maximum decrease threshold and continues to fall below the demand heart rate threshold 604 and the life sustaining threshold 608. In this case, the active energy level 610 may once again be instantaneously increased to the enhanced energy level and post shock pacing therapy 614 may be delivered until point D, where the intrinsic heart rate 602 rises above the demand heart rate threshold 604. In some cases, the post shock pacing therapy 614 may be delivered for a predetermined period of time or until the intrinsic heart rate 602 has stabilized. Once again, in this example, because the intrinsic heart rate 602 did not rise above the upper limit threshold 606 before it started falling at a rate above the maximum decrease threshold, the active energy level 610 may be decreased back to the first energy level once the intrinsic heart rate 602 has stabilized (or after a predetermined period of time). However, it is contemplated that the active energy level 610 may remain at the enhanced energy level for a period of time.

At point E, the intrinsic heart rate 602 has fallen below the demand heart rate threshold 604. In this example, demand pacing therapy 612 is delivered at the first energy level until point F, where the intrinsic heart rate 602 rises above the demand heart rate threshold 604. After point F, the active energy level 610 is still set at the first energy level as the intrinsic heart rate 602 continues to rise.

Figure 6D:
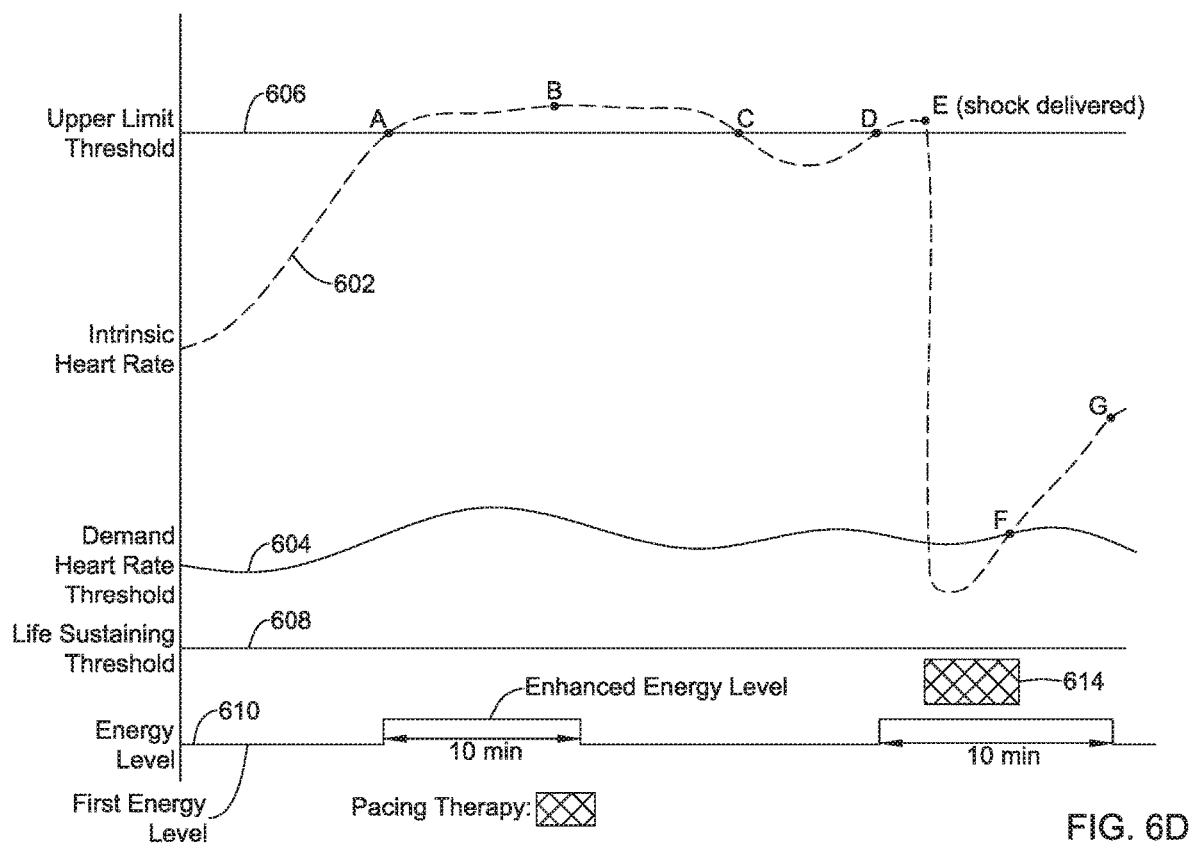

Turning now to FIG. 6D, the initial intrinsic heart rate 602 is below the upper limit threshold 606 and the intrinsic heart rate 602 is not falling at a rate that is above the maximum decrease threshold. As a result, the active energy level 610 may be set at a first energy level at which the LCP delivers pacing pulses. As shown in FIG. 6D, the intrinsic heart rate 602 rises to the upper limit threshold 606 at point A. In response, and in this example, the active energy level 610 may be increased to the enhanced energy level for a 10 minute time period. At point B, the 10 minute time period has expired and the intrinsic heart rate 602 remains above the upper limit threshold 606. In this example, the active energy level 610 may decrease back to the first energy level even though the intrinsic heart rate 602 has not yet fallen below the upper limit threshold 606. At point C, the intrinsic heart rate 602 falls below the upper limit threshold 606. At point D, the intrinsic heart rate 602 once again rises to the upper limit threshold 606 and the active energy level 610 may once again be increased to the enhanced energy level for the 10 minute time period. At point E, the intrinsic heart rate 602 starts falling at a rate that is above the maximum decrease threshold. This may indicate that an ICD may have delivered a shock to the patient's heart. As a result, the post shock pacing therapy 614 may be delivered at the enhanced energy level. As shown in FIG. 6D, the post shock pacing therapy 614 may be delivered until point F, where the intrinsic heart rate 602 rises above the demand heart rate threshold 604. In some cases, the post shock pacing therapy 614 may be delivered for a predetermined period of time or until the intrinsic heart rate 602 has stabilized. The active energy level 610 may not decrease back to the first energy level until point G, when the 10 minute time period has expired.

Figure 6E:
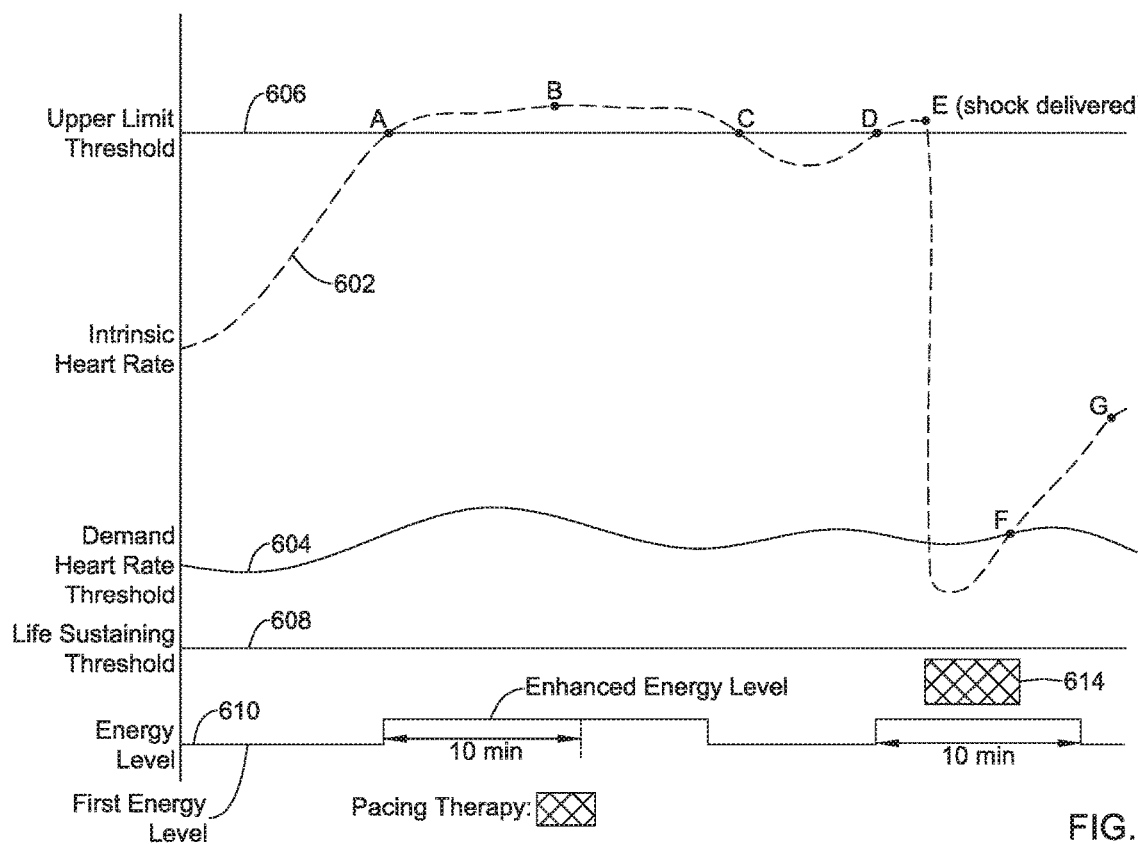

Turning now to FIG. 6E, the initial intrinsic heart rate 602 is below the upper limit threshold 606 and the intrinsic heart rate 602 is not falling at a rate that is above the maximum decrease threshold. As a result, the active energy level 610 may be set at a first energy level at which the LCP delivers pacing pulses. As shown in FIG. 6E, the intrinsic heart rate 602 rises to the upper limit threshold 606 at point A. In response, the active energy level 610 may be increased to the enhanced energy level for a 10 minute time period as shown. At point B, the 10 minute time period has expired and the intrinsic heart rate 602 remains above the upper limit threshold 606. In this example, the active energy level 610 remains at the enhanced energy level even though the 10 time period has expired. At point C, the intrinsic heart rate falls below the upper limit threshold 606 and the active energy level 610 is now decreased back to the first energy level. At point D, the intrinsic heart rate 602 once again rises to the upper limit threshold 606 and the active energy level 610 may once again be increased to the enhanced energy level for another 10 minute time period. At point E, the intrinsic heart rate 602 starts falling at a rate that is above the maximum decrease threshold. This may indicate that an ICD may have delivered a shock to the patient's heart. As a result, post shock pacing therapy 614 may be delivered at the enhanced energy level. As shown in FIG. 6E, the pacing therapy 612 may be delivered until point F, where the intrinsic heart rate 602 rises above the demand heart rate threshold 604. In some cases, the post shock pacing therapy 614 may be delivered for a predetermined period of time or until the intrinsic heart rate 602 has stabilized. The active energy level 610 may not decrease back to the first energy level until point G, when the 10 minute time period has expired.

Figure 6F:
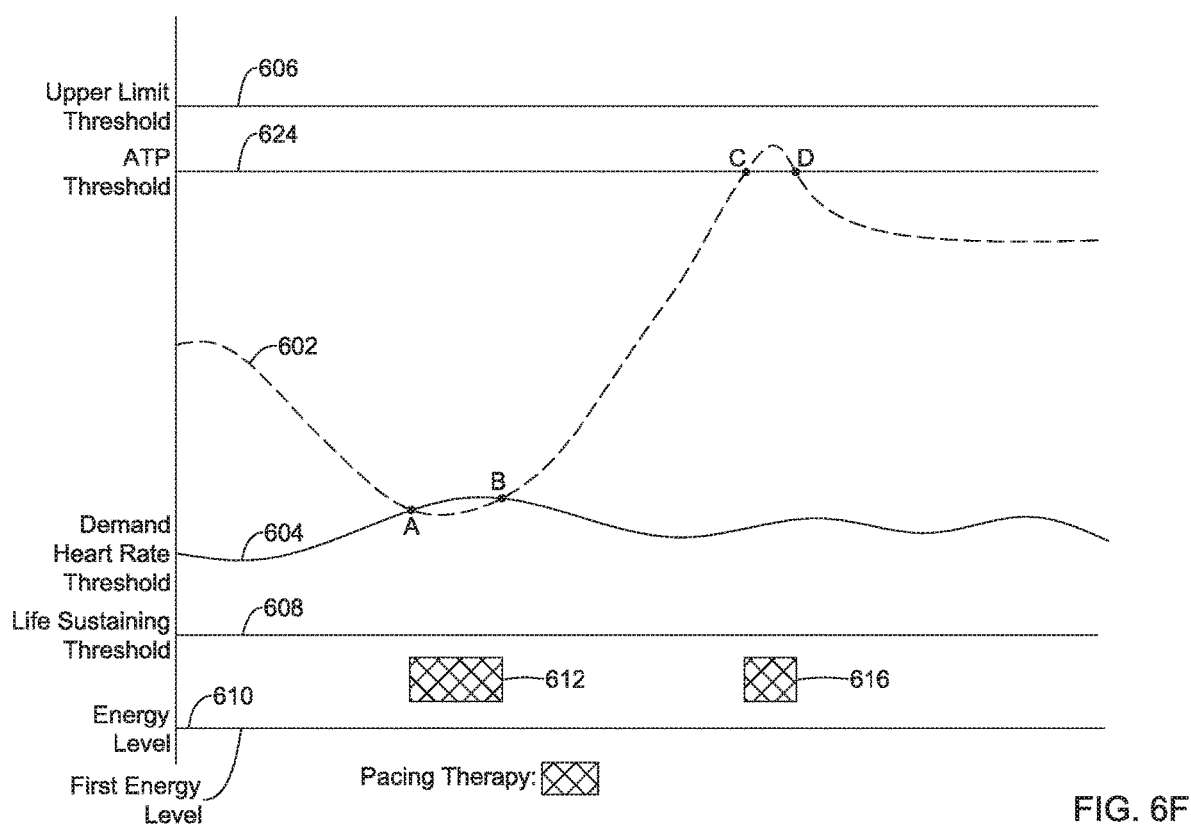

Turning now to FIG. 6F, the intrinsic heart rate 602 is initially below the upper limit threshold 606 and the intrinsic heart rate 602 is not falling at a rate that is above a maximum decrease threshold. As a result, the LCP may set the active energy level 610 at which the LCP would deliver pacing pulses to the first energy level. The intrinsic heart rate then falls below the demand heart rate threshold 604 at point A. As shown in FIG. 6F, demand pacing therapy 612 is delivered at the first energy level until point B, where the intrinsic heart rate 602 rises above the demand heart rate threshold 604. This is an example of demand pacing, which helps ensure that the heart rate of a patient does not fall below a lower heart rate threshold such as the demand heart rate threshold 604. When performing demand pacing, the LCP may pace the heart at the lower heart rate threshold (e.g. demand heart rate threshold 604) when the intrinsic heart rate falls below the lower heart rate threshold (e.g. demand heart rate threshold 604).

After point B, the active energy level 610 is still set at the first energy level as the intrinsic heart rate 602 continues to rise. At point C, the intrinsic heart rate 602 has reached the ATP threshold 624. As shown in FIG. 6F, ATP therapy 616 is delivered at the first energy level until point D, where the intrinsic heart rate 602 falls below the ATP threshold 624. This is an example of ATP therapy that was effective at terminating a tachyarrhythmia, which helps ensure that the heart rate of the patient does not rise above a higher heart rate threshold such as the ATP threshold 624. When performing ATP therapy, the LCP may pace the heart with a burst of pulses.

Figure 6G:
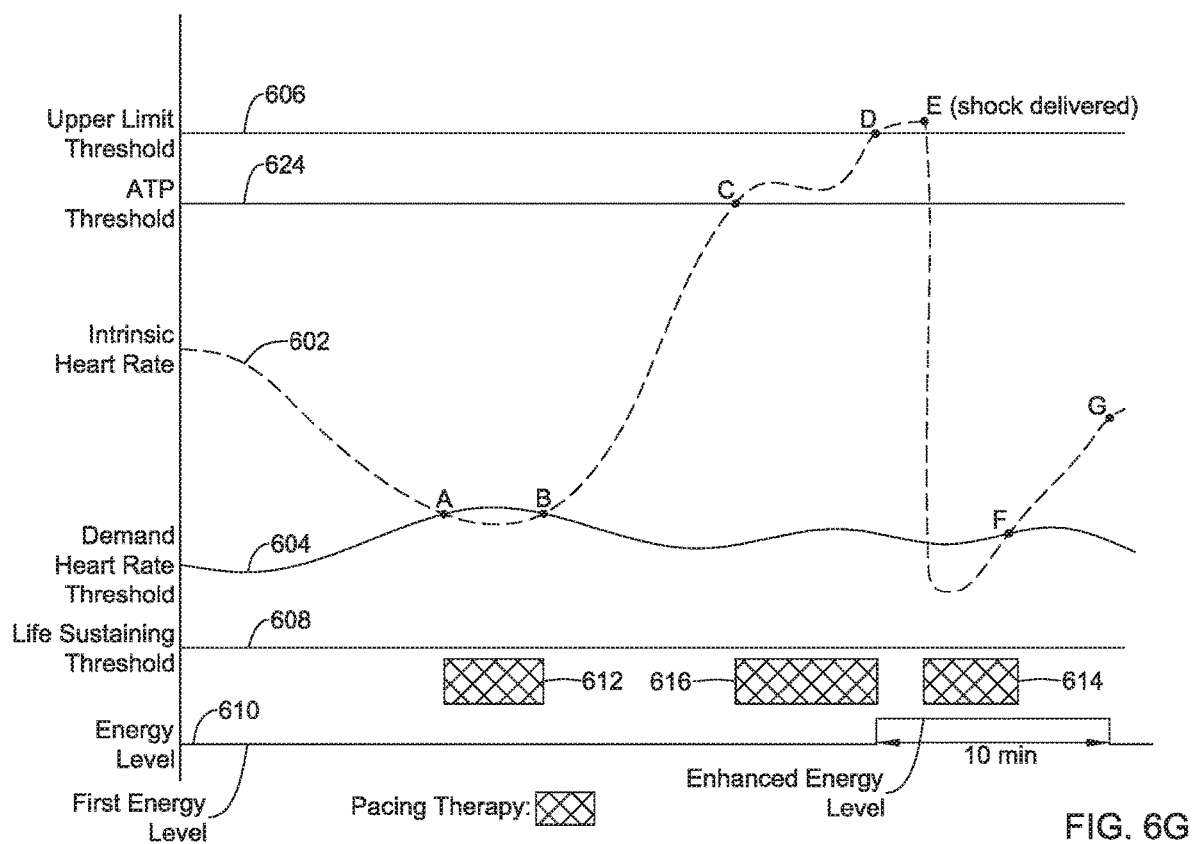

Turning now to FIG. 6G, the intrinsic heart rate 602 is initially below the upper limit threshold 606 and the intrinsic heart rate 602 is not falling at a rate that is above a maximum decrease threshold. As a result, the LCP may set the active energy level 610 at which the LCP would deliver pacing pulses to the first energy level. The intrinsic heart rate then falls below the demand heart rate threshold 604 at point A. As shown in FIG. 6F, demand pacing therapy 612 is delivered at the first energy level until point B, where the intrinsic heart rate 602 rises above the demand heart rate threshold 604. After point B, the active energy level 610 is still set at the first energy level as the intrinsic heart rate 602 continues to rise. At point C, the intrinsic heart rate 602 has reached the ATP threshold 624 and ATP therapy 616 is delivered. In some cases, the ATP therapy 616 may not be capable of terminating the tachyarrhythmia and bringing the intrinsic heart rate 602 below the ATP threshold 624. In some cases, as shown in FIG. 6G, the intrinsic heart rate 602 may continue to rise and at point D, reach the upper limit threshold 606. At point D, the LCP may stop delivering the ATP therapy 616 at the first energy level and the active energy level 610 may be increased to the enhanced energy level for a 10 minute time period, which might be extended as described above. At point E, the intrinsic heart rate 602 starts falling at a rate that is above the maximum decrease threshold. This may indicate that an ICD has delivered a shock to the patient's heart. As a result, the LCP may be configured to deliver post shock pacing therapy 614 at the enhanced energy level. As shown in FIG. 6G, the post shock pacing therapy 614 may be delivered until point F, where the intrinsic heart rate 602 rises above the demand heart rate threshold 604. In response, and in some cases, post shock pacing therapy 614 may be delivered for a predetermined period of time or until the intrinsic heart rate 602 has stabilized. Even though the post shock pacing therapy 614 is no longer being delivered after point F, in this example, the active energy level 610 may not decrease back to the first energy level until point G, when the 10 minute window has expired.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A cardiac pacemaker that is free from an Implantable Cardioverter Defibrillator (ICD) that is configured to provide defibrillation therapy, the cardiac pacemaker comprising:
   one or more sensors for sensing one or more physiological parameters of a patient;
   two or more pacing electrodes for delivering pacing pulses to the heart of the patient;
   electronics operatively coupled to the one or more sensors and the two or more pacing electrodes, the electronics configured to:
      determine a heart rate of the patient based at least in part on the one or more physiological parameters sensed by the one or more sensors;
      pace the heart of the patient via the two or more pacing electrodes in a manner that attempts to keep the heart rate of the patient from falling below a demand heart rate threshold, wherein:
         the pacing pulses are delivered at a capture pacing energy level; and
         when the heart rate rises above an upper heart rate threshold, then for a temporary period of time, the pacing pulses are delivered at an enhanced energy level above the capture pacing energy level regardless of whether defibrillation therapy is delivered or not.

2. The cardiac pacemaker of claim 1, wherein the one or more sensors comprises two or more sensing electrodes, and at least one of the physiological parameters comprises a cardiac electrical signal.

3. The cardiac pacemaker of claim 1, wherein at least one of the two or more sensing electrodes is one of the pacing electrodes.

4. The cardiac pacemaker of claim 1, wherein the one or more sensors comprise an accelerometer, and at least one of the physiological parameters comprises one or more of a heart motion and a heart sound.

5. The cardiac pacemaker of claim 1, wherein the heart rate determined by the electronics is an average heart rate of "n" previous heart beats, wherein "n" is an integer greater than one.

6. The cardiac pacemaker of claim 1, wherein the pacing pulses have a first amplitude and first pulse width at the capture pacing energy level, and a second amplitude and second pulse width at the enhanced energy level, wherein the second amplitude is greater than the first amplitude and the second pulse width is the same as the first pulse width.

7. The cardiac pacemaker of claim 1, wherein the pacing pulses have a first amplitude and first pulse width at the capture pacing energy level, and a second amplitude and second pulse width at the enhanced energy level, wherein the second amplitude is the same as the first amplitude and the second pulse width is greater than the first pulse width.

8. The cardiac pacemaker of claim 1, wherein the pacing pulses have a first amplitude and first pulse width at the capture pacing energy level, and a second amplitude and second pulse width at the enhanced energy level, wherein the second amplitude is greater than the first amplitude and the second pulse width is greater than the first pulse width.

9. The cardiac pacemaker of claim 1, wherein the period of time is a predetermined period of time.

10. The cardiac pacemaker of claim 9, wherein the predetermined period of time is programmable.

11. The cardiac pacemaker of claim 1, wherein the period of time is greater than 3 minutes.

12. The cardiac pacemaker of claim 1, wherein the period of time is less than 1 hour.

13. The cardiac pacemaker of claim 1, further comprising a communication module, wherein the electronics can receive commands from a remote device via the communication module, and wherein in response to receiving an ATP command, the electronics is configured to deliver a burst of ATP pacing pulses at the enhanced energy level.

14. The cardiac pacemaker of claim 1, wherein the cardiac pacemaker is a leadless cardiac pacemaker (LCP) that is configured to be implanted within a chamber of the heart of the patient.

15. A leadless cardiac pacemaker (LCP) comprising:
   a housing;
   a plurality of electrodes for sensing electrical signals emanating from outside of the housing;
   an energy storage module disposed within the housing;
   a pulse generator for delivering pacing pulses via two or more of the plurality of electrodes, wherein the pulse generator is capable of changing an energy level of the pacing pulses;
   a control module disposed within the housing and operatively coupled to the pulse generator and at least two of the plurality of electrodes, wherein the control module is configured to:
      receive one or more cardiac signals via two or more of the plurality of electrodes;

determine a heart rate based at least in part on the received one or more cardiac signals;

instruct the pulse generator to pace the heart with pacing pulses of a capture pacing energy level in a manner that attempts to keep the heart rate from falling below a demand heart rate threshold;

determine if the heart rate rises above an upper heart rate threshold; and in response to determining that the heart rate has risen above the upper heart rate threshold, regardless of whether any defibrillation therapy has been or will be initiated by a remote device, instruct the pulse generator to increase the energy level of the pacing pulses to an enhanced energy level for a temporary period of time, and after the temporary period of time, instruct the pulse generator to decrease the energy level of the pacing pulses back to the capture pacing energy level.

16. The LCP of claim 15, wherein the pulse generator changes an amplitude of the pacing pulses to increase the energy level of the pacing pulses to the enhanced energy level.

17. The LCP of claim 15, wherein the pulse generator changes a pulse width of the pacing pulses to increase the energy level of the pacing pulses to the enhanced energy level.

18. The LCP of claim 15, wherein the pulse generator changes an amplitude and a pulse width of the pacing pulses to increase the energy level of the pacing pulses to the enhanced energy level.

19. A method for pacing a heart of a patient, the method comprising:

determining a heart rate of the patient;

pacing the heart of the patient in a manner that attempts to keep the heart rate of the patient from falling below a demand heart rate threshold, wherein:

the pacing pulses are delivered at a capture pacing energy level; and when the heart rate rises above an upper heart rate threshold, then for a period of time after rising above the upper heart rate threshold and beginning before any defibrillation shocks are delivered to the heart in response to the rising heart rate, delivering pacing pulses at an enhanced energy level above the capture pacing energy level.

20. The method of claim 19, wherein the heart rate determined by an average heart rate of "n" previous heart beats, wherein "n" is an integer greater than one.

* * * * *